US008716533B2

(12) United States Patent
Tuinstra et al.

(10) Patent No.: US 8,716,533 B2
(45) Date of Patent: May 6, 2014

(54) METHODS OF SAPONIFYING XANTHOPHYLL ESTERS AND ISOLATING XANTHOPHYLLS

(75) Inventors: Joshua James Tuinstra, Plainwell, MI (US); Gregory S. Reynhout, Kalamazoo, MI (US); James Barren, Kalamazoo, MI (US)

(73) Assignee: Kalamazoo Holdings, Inc., Kalamazoo, MI (US)

( * ) Notice: Subject to any disclaimer, the term of this patent is extended or adjusted under 35 U.S.C. 154(b) by 0 days.

(21) Appl. No.: 13/322,674

(22) PCT Filed: May 28, 2010

(86) PCT No.: PCT/US2010/001587
§ 371 (c)(1),
(2), (4) Date: Jan. 9, 2012

(87) PCT Pub. No.: WO2010/138210
PCT Pub. Date: Dec. 2, 2010

(65) Prior Publication Data
US 2012/0107380 A1 May 3, 2012

Related U.S. Application Data

(60) Provisional application No. 61/217,331, filed on May 29, 2009.

(51) Int. Cl.
*C07C 35/21* (2006.01)
(52) U.S. Cl.
USPC ........................................................ 568/816
(58) Field of Classification Search
USPC ........................................................ 568/816
See application file for complete search history.

(56) References Cited

U.S. PATENT DOCUMENTS

| | | |
|---|---|---|
| 2,849,507 A | 8/1958 | Isler |
| 3,206,315 A | 9/1965 | Klaui |
| 3,206,316 A | 9/1965 | Heinrich |
| 3,441,623 A | 4/1969 | Surmatis |
| 3,523,138 A | 8/1970 | Grant |
| 3,989,757 A | 11/1976 | Surmatis |
| 4,883,887 A | 11/1989 | Bernhard |
| 5,382,714 A | 1/1995 | Khachik |
| 5,523,494 A | 6/1996 | Torres-Cardona |
| 5,602,286 A | 2/1997 | Muralidhara |
| 5,648,564 A | 7/1997 | Ausich |
| 5,847,238 A | 12/1998 | Muralidhara |
| 5,876,782 A | 3/1999 | Sas |
| 5,876,792 A | 3/1999 | Sas |
| 5,973,211 A | 10/1999 | Rodriguez |
| 5,998,678 A | 12/1999 | Sanroma |
| 6,110,478 A | 8/2000 | Harang |
| 6,191,293 B1 | 2/2001 | Levy |
| 6,221,417 B1 | 4/2001 | Sas |
| 6,262,284 B1 | 7/2001 | Khachik |
| 6,329,432 B2 | 12/2001 | Howard |
| 6,329,557 B1 | 12/2001 | Rodriguez |
| 6,376,722 B1 | 4/2002 | Sanz |
| 6,380,442 B1 | 4/2002 | Madahavi |
| 6,504,067 B1 | 1/2003 | Montoya |
| RE38,009 E | 2/2003 | Garnett |
| 6,743,953 B2 | 6/2004 | Kumar |
| 6,747,177 B2 | 6/2004 | Ernst et al. |
| 6,784,351 B2 | 8/2004 | Hauptmann |
| 6,797,303 B2 | 9/2004 | Zelkha |
| 7,109,361 B2 | 9/2006 | Hoffman |
| 7,150,890 B2 | 12/2006 | Rosales |
| 7,173,145 B2 | 2/2007 | Khachik |
| 7,179,930 B2 | 2/2007 | Bhaskaran |
| 7,691,406 B2 | 4/2010 | Garnett et al. |
| 2003/0108598 A1 | 6/2003 | Garnett |
| 2005/0139145 A1 | 6/2005 | Quesnel |
| 2006/0185034 A1 | 8/2006 | Todd, Jr. |
| 2007/0032683 A1 | 2/2007 | Xu |
| 2007/0161826 A1 | 7/2007 | Pena |

FOREIGN PATENT DOCUMENTS

| | | |
|---|---|---|
| CN | 1436774 | 8/2003 |
| ES | 2265787 | 2/2007 |
| JP | 57133160 | 8/1982 |
| JP | 57180663 | 11/1982 |
| JP | 58173164 | 10/1983 |
| WO | WO 97/23436 | 7/1997 |
| WO | WO0016792 | 3/2000 |
| WO | WO 01/94279 | 12/2001 |
| WO | WO02060865 | 8/2002 |
| WO | WO 2004/018417 | 3/2004 |
| WO | WO 2006/114794 | 11/2006 |

OTHER PUBLICATIONS

International Search Report for PCT/US2010/001587 dated Jul. 28, 2010.
Written Opinion of the International Searching Authority for PCT/US2010/001587 of May 28, 2010.
Chopra, et al. Effect of Lutein on Oxidation of Low Density Lipoproteins (LDL) in vitro. Human Nutrition Research Group; University of Ulster, Coleraine, BT52 1SA; Abtracts of Communications, 18A, 1993.
Craft, et al. Journal of Agric. Food Chem. 40:431-434, 1992.
Howard, et al. Internat. J. Vit. Nutr. Res. 66:113-118, 1996.

(Continued)

Primary Examiner — Brian J Davis
(74) Attorney, Agent, or Firm — Hueschen and Sage (57) ABSTRACT

This invention relates to a practical and effective process for converting esterified xanthophylls, including zeaxanthin, to non-esterified xanthophylls through saponification. In addition, the invention provides a process for obtaining esterified zeaxanthin in high yields and purities, isolating the xanthophylls from interfering substances such as waxes, oils, and fats. A product of this process is a zeaxanthin rich substrate that is suitable for use in foods, nutritional supplements, cosmetics, pharmaceuticals and related products.

34 Claims, 2 Drawing Sheets

(56) References Cited

OTHER PUBLICATIONS

Khachik Journal of Chromatography 582:153-166, 1992.
Roberts, et al. Clinics in Dermatology, 27:195-201, 2009.
Schieber, et al. Trends in Food Science and Technology, 16:416-422, 2005.
Abel, Robert Jr. The Eye Care Revolution Kensington Publishing Corp. New York, New York, Chapter 8, p. 158, 1999.
Ahmed, et al. Survey of Opthamology 50:183-193, 2005.
Alves-Rodriguez, et al. Toxicology Letters 150:57-83, 2004.
Beatty, et al. Archives of Biochemistry and Biophysics 430:70-76, 2004.
Brown, et al. American Society for Clinical Nutrition 70:517-24, 1999.
Chew, et al. Anticancer Research 16:3689-3694, 1996.
Conner, et al. Journal of the American Dietetic Association. 104:1793-1799, 2004.
Curl Agricultural and Food Chemistry 1:456-460, 1953.
Curl Agricultural and Food Chemistry 10:504-509, 1962.
Curl Agricultural and Food Chemistry 12:522-524, 1964.
Davies, et al. Progress in Retinal Eye Research 23:533-559, 2004.
Englert, et al. Helvetica Chemica Acta 74:969-982, 1991.
Granado, et al. J. Agric. Food Chem. 40:2135-2140, 1992.
Granado, et al. Journal of Food Composition and Analysis 14:474-489, 2001.
Hart, et al. Food Chemistry 54:101-111, 1995.
Isler, et al. Volumen XXXIX, Fasciculus X, No. 27, pp. 249-259, 1956.
Ito. et al. Journal of Epidemiology vol. 15 (Supplement II) S140-S149, 2005.
Karrer, et al. Chapter V, pp. 38-42, in Carotenoids, Elsevier Publishing Co., Inc. Amsterdam, 1950.
Khachik, et al. J. Agric. Food Chem. 34:603-616, 1986.
Khachik, et al. Journal of Cellular Biochemistry (Supplement) 22:236-246, 1995.
Kimura, et al. Food Chemistry 35:187-195, 1990.
Kohlmeier, et al. Am J Clin Nutr (Supplement) 62:1370S-1376S, 1995.
Larsen, et al. J. Agric. Food Chem. 53:6598-6602, 2005.
Levy, et al. Nutrition and Cancer 24:257-266, 1995.
Lyle, et al. American Journal of Epidemiology 149:801-809, 1999.
Minguez-Mosquera, et al. J. Agric. Food Chem. 41:1616-1620, 1993.
Moeller, et al. Journal of the American College of Nutrition 19:522S-527S, 2000.
Morris, et al. JAMA 272:1439-1441, 1994.
Murakoshi, et al. Cancer Research 52:6583-6587, 1992.
Pattison, et al. American Journal of Clinical Nutrition 82:451-455, 2005.
Ribaya-Mercado, et al. Journal of the American College of Nutrition 23:567S-587S, 2004.
Roche Roche Vitamins Technical Publication HHN-1382/0800, 2000.
Rock, et al. Journal of Clinical Oncology 23:6631-6638, 2005.
Rodriguez-Bernaldo, et al. Journal of Food Composition and Analysis 19:97-111, 2006.
Scott Food Chemistry 45:357-364, 1992.
Seddon, et al. JAMA 272:1413-1420, 1994.
Stahl Nutrition and the Eye, in Dev. Opthamol. Karger Publishers, Basel Switzerland, vol. 38, pp. 70-88, 2005.
Stringham, et al. Nutrition Reviews 63:59-64, 2005.
Tanaka, et al. Carcinogenesis 15:15-19, 1994.
Tyczkowski, et al. Poultry Science 70:651-654, 1990.
Updike, et al. J. Agric. Food Chem. 1:6184-6190, 2003.
U.S. Appl. No. 12/800,416, Office Action dated Feb. 14, 2012.
Wingerath, et al. Archives of Biochemistry and Biophysics 324:385-390, 1995.
Zechmeister, L Cis-Trans Isomeric Carotenoids Vitamins A and Arylpolyenes. Academic Press Publishers, New York, New York, pp. 46-47, 1962.
International Preliminary Report on Patentability for PCT/US2010/01587 of Jan. 31, 2012.

Figure 1. (Prior Art) The chemical structures of zeaxanthin and lutein.

Zeaxanthin

Lutein

Figure 2: Isomerizing *cis* isomers to *trans* isomers at room temperature over time and the effect on yield recovery.

METHODS OF SAPONIFYING XANTHOPHYLL ESTERS AND ISOLATING XANTHOPHYLLS

FIELD OF THE INVENTION

This invention relates to a practical and effective process for converting esterified xanthophylls, including zeaxanthin, to non-esterified xanthophylls through saponification. In addition, the invention provides a process for obtaining esterified zeaxanthin in high yields and purities, isolating the xanthophylls from interfering substances such as waxes, oils, and fats. The process employs hydrolysis (saponification) of xanthophyll esters in a mixture of isopropyl alcohol, water, and alkali to separate the xanthophylls from impurities. A product of this process is a zeaxanthin rich substrate that is suitable for use in foods, nutritional supplements, cosmetics, pharmaceuticals and related products.

BACKGROUND OF THE INVENTION

The present invention relates to xanthophylls that have beneficial health effects in humans and other animals and more particularly to zeaxanthin and its production.

Xanthophylls are oxygenated carotenoids that are widely distributed in nature. Although xanthophylls are present in green vegetables, yellow/orange fruits and vegetables, and various bacteria, a *Capsicum* genus provides one of the richest, whole food sources of xanthophylls and other carotenoids, found in nature. The ripe fruit of the *Capsicum* genus often contains an ample source of capsanthin, capsorubin, cryptoxanthin, zeaxanthin, lutein, and other carotenoids that have substantial nutritional and medicinal value. The xanthophylls are usually found as mixtures of diesters and monoesters of fatty acids containing anywhere from about eight to twenty-two carbon atoms. Examples of these fatty acids include linoleic, palmitic, oleic, linolenic, myristic, stearic, lauric, and the like.

In recent years a number of human and animal studies have indicated various beneficial effects of xanthophylls, especially zeaxanthin and lutein. Zeaxanthin and lutein, and only these two dietary xanthophylls, occur in high concentration in the retina of the eye. Zeaxanthin is more highly concentrated at the center of the macula and protects the macula from the damaging, photo-oxidative effects of short-wave ultra violet radiation. A higher dietary intake of carotenoids is also associated with a lower risk for AMD (Age-related Macular Degeneration) occurring in older adults. Hereditary forms with an early onset include Stargardts, Best's Disease and progressive Cone Dystrophy. Hereditary retinal degenerations that attack the whole of the retina tend to be more severe. The most common types of these diseases are Retinitis Pigmentosa, Choroideremia, Ushers Syndrome and diabetic retinopathy. individuals consuming the highest levels of carotenoids exhibit a 43% (statistically significant) lower risk for AMD. The specific carotenoids, zeaxanthin and lutein, are most strongly associated with a reduced risk for AMD (Seddon et al., 1994). Other health benefits include anti-cancer activity, antioxidant function in cardiovascular disease prevention (Howard et al., 1996), control over LDL cholesterol (Chopra et al., 1994), as well as many other health benefits (Roberts et al., 2009).

Zeaxanthin ($\beta,\beta$-carotene-3,3'-diol) exists in three stereoisomeric forms: the (3R,3'R) stereoisomer is the principle form occurring in plants as well as in the human and mammalian eye, the (3R,3'S) form is called meso-zeaxanthin, and there is also a third (3S,3'S) form. Given the number of double bonds in this structure a large number of cis isomers are possible. The major cis forms have been identified in the human retina, but the preferred bio-available form is trans isomer (3R, 3'R) as evidenced from the data of a geometric isomer compositional analysis of human plasma. (Khachik et al., 1992). All three stereoisomers have been found in the human retina (Howard, et al., U.S. Pat. No. 6,329,432), but the 3R, 3'R isomer is dominant.

A highly purified and concentrated source of natural zeaxanthin is needed for the manufacture of dietary supplements, functional foods and cosmetic applications. Moreover, zeaxanthin is an important ingredient to add color to foods and as an additive in animal feeds to color poultry skin, egg yolks, fish flesh and the like. A natural source of zeaxanthin that can be used in foods is preferred and/or regulated over a synthetic product in these applications.

Beverages, including but not limited to, nutritional drinks, sodas, beer, alcoholic beverages, fruit juices (including, but not limited to orange juice, apple juice, grape juice, cranberry juice, tomato juice, guava juice, mango juice, cantaloupe juice, carrot juice, and grapefruit juice), dairy beverages, soy beverages, infant formulas, adult formulas, and their concentrates can be colored or fortified with a highly purified and concentrated zeaxanthin product.

Highly purified and concentrated zeaxanthin may be used in various types of cosmetic applications. It can be applied topically or taken internally for sun protection and as an antioxidant. Zeaxanthin can be used in lip applications such as lip balms, lipsticks, lip liners, lip moisturizers, and the like. Zeaxanthin may be used in cosmetic applications that include foundations, makeup, blushes, tanning creams, and the like. It can also be used in topical products that are applied to the skin for protection from the effects of radiation, such as that from the sun. These products include tanning lotions, tanning accelerators, tanning moisturizers, and the like. An example of using zeaxanthin in cosmetic applications is U.S. Pat. No. 6,110,478, which discloses a composition for cosmetic purposes which is a regulator of cutaneous pigmentation and is adapted both to administration by the oral route and to application on the skin.

A highly purified and concentrated zeaxanthin may be in a form selected from powders, beadlets, water-dispersible powders, crystals, amorphous solids, encapsulated solids and microencapsulated solids. Zeaxanthin may be placed into microcapsules for protection from heat, light, and oxidation. These microcapsules may also be suitable for use in human or animal foods, multivitamins, dietary supplements, and personal care products.

Zeaxanthin can be manufactured synthetically by the Wittig reaction in a multi-step process (Ernst et al., U.S. Pat. No. 6,747,177). The synthetic manufacture of zeaxanthin involves the use of multiple steps, including catalytic hydrogenations, chemical reductions and other steps that don't satisfy the market needs for an all-natural, whole food source of zeaxanthin as provided by this invention. There is a need in the marketplace for a naturally derived form of zeaxanthin, as opposed to synthetic zeaxanthin, that can serve as a dietary source in the form of dietary supplements, food or beverage additives, or food or beverage colorants. In addition, there also is a need in the marketplace for the naturally derived form to be obtained from a whole food source, such as a fruit or vegetable, as opposed to a non-whole food source such as a flower or bacteria.

Several patents and publications describe the isolation of xanthophylls, mainly zeaxanthin and lutein, from plant sources on a commercial scale. Many of these teachings focus on the isolation of lutein from marigold flower petals.

Figure 1:
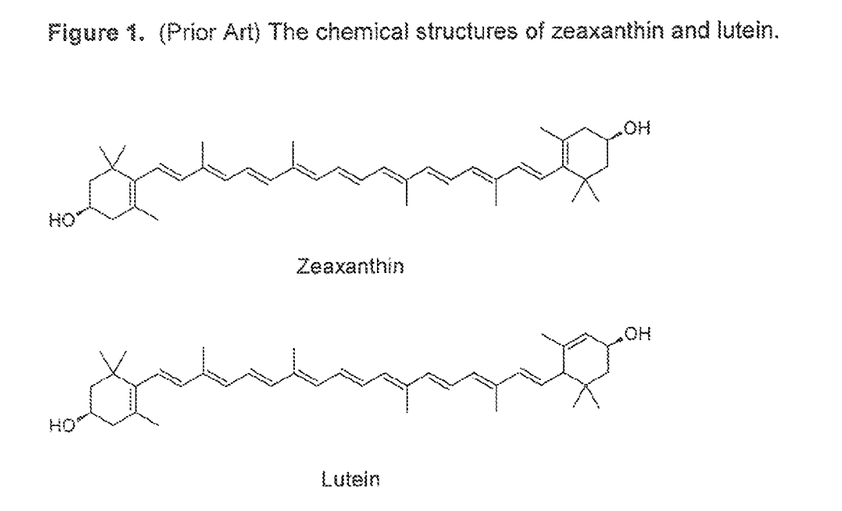
FIG. 1. The chemical structures of zeaxanthin and lutein are shown.

There is considerable art describing the saponification of lutein esters. Although zeaxanthin and lutein share certain chemical features (FIG. 1), these compounds show considerable differences in solubility (Table 1). Simply applying well-known lutein saponification process conditions to zeaxanthin can be problematic due to the differences in solubility between these two materials. Therefore it is not practical to apply generic xanthophyll teachings that require dissolution of zeaxanthin in a solvent as a key step. Such a process applied to zeaxanthin would require excessive amounts of solvents in some cases, or the use of problematic solvents such as tetrahydrofuran or dichloromethane.

An embodiment of this invention is to provide a process that is practical and effective for isolating zeaxanthin in non-esterified form from a whole food source such as a *Capsicum* species. As mentioned previously, simply applying lutein process conditions to zeaxanthin can be problematic due to the differences in solubility of these two materials (see Table 1). One must also consider the differences in the concentrations of the carotenoids in their respective matrices, and the nature of the matrices themselves. It is therefore not helpful that the prior art related to industrial scale production of generic xanthophylls teaches steps that would require the dissolution of zeaxanthin in a solvent, when this compound has limited solubility in many non-polar and polar solvents. This latter point especially pertains to alcohols, which are often preferred solvents for saponification.

Reilly, et al., U.S. application Ser. No. 12/800,416 provide a method that uses an alcohol and hydrocarbon to isolate xanthophylls, in particular zeaxanthin, using various partitions and multiple methanol washes to reach the desired purity. The starting material, reaction conditions, and solvent ratios greatly affect the partitioning characteristics and the time required for efficient partitioning of the product. The process generates mixed solvent streams, recovery of which is problematic. The present invention does not rely on partitions described in Reilly, et al., U.S. application Ser. No. 12/800,416.

Reilly, et al., U.S. application Ser. No. 12/800,416 provide an excellent review of many prior art patents and other references that use procedures to isolate xanthophylls. Neither this patent application, nor the art cited therein describe or anticipate the present invention.

Madhavi, et al. (U.S. Pat. No. 6,380,442) describe a method for producing a lutein enriched product from marigold flower extract. In this process, isopropyl alcohol, water, and alkali are used to separate and precipitate out lutein from marigold flower oleoresin. The method does not describe a method for the isolation of zeaxanthin. Nor does it employ a process that promotes large crystal formation for easier removal and washing that will result in higher yields and purities. Madhavi, et al. (U.S. Pat. No. 6,380,442) also require 1-4 hours of settling after the reaction is complete and two additional dilution steps prior to isolation of the solid product. We have found their conditions inadequate to produce the high isolated yields and high purities of the current invention, as described in this specification and the examples. Madhavi, et al. (U.S. Pat. No. 6,380,442) require water dilution steps that increase the volume of the reaction mixture, creating larger and more dilute volumes that must be processed to isolate the desired product. Such dilution steps are not needed in the present invention. Madhavi, et al. (U.S. Pat. No. 6,380, 442) fail to describe a process for collecting additional total xanthophyll yield once the initial isolation is complete. The present invention describes a method of collecting additional zeaxanthin from the reaction supernatant after filtration of the initial product. Adapting the teachings of Madhavi, et al. to the isolation of zeaxanthin from *Capsicum* oleoresin resulted in very poor yields (~31%). The additional yield of the present invention results in large part from the conversion of the more soluble cis isomer to the less soluble trans isomer, which after exceeding its' solubility limit, precipitates out over time. Madhavi, et al. (U.S. Pat. No. 6,380,442) do not employ a process that isolates the desired trans zeaxanthin from a whole food source, nor do they describe certain process variables that are taught in the present invention. Refer to Example 7 for more details.

Quesnel, et al. (E.P. 1,371,641 A1, W.O. 03/104190 A1, and U.S. Published Application No. 2005/1039145) describe a method for isolating carotenoid crystals from a plant oleoresin which uses a hydrocarbon solvent, an alcohol, and a base. The invention requires the use of partitioning and generates mixed solvents streams that are costly on a commercial scale to recover and separate.

Sanz, et al. (W.O. 99/23067) teach a process of isomerizing lutein to zeaxanthin using a catalyst. Catalysts are costly and not needed in the present invention to obtain a zeaxanthin product. This patent requires the use of high temperatures for the conversion, which if used in the context of isolating zeaxanthin from a *Capsicum* source, would cause isomerization of trans zeaxanthin to the more soluble cis isomer and result in unacceptably lower recovery and yields.

Muralidhara, et al. (U.S. Pat. No. 5,847,238) describe a process for recovering xanthophylls from corn gluten by means of saponification and purifying the crude xanthophylls by means of partition adsorption chromatography, ion exchange chromatography, size exclusion chromatography or countercurrent chromatography. These isolation technologies are expensive and not needed in the present invention.

Ferrater, et al. (E.S. 2,265,787) describe a method for treating carotenoid oleoresins with an alkaline reagent and heating to temperatures between 150-190° C., followed by spray drying. Again, this invention uses high temperatures that would degrade and isomerize the zeaxanthin to the less desired cis isomer that is more difficult to isolate.

Xu, et al. (C.N. 1,436,774 A1) describes a process for extracting lutein from marigolds, saponifying the extract, and recrystallizing the resulting material in tetrahydrofuran/water/n-hexane or petroleum ether. This process uses solvents that are potentially dangerous and not suitable for food additives or nutritional supplements.

Ausich, et al. (W.O. 97/23436 A1) provide a method for isolation and purification of xanthophylls, preferably lutein from marigold flower petals, zeaxanthin from wolfberries or capsanthin and capsorubin from red pepper, with the composition of propylene glycol and aqueous alkali.

Swaminathan, et al. (W.O. 2006/114794 A1) provide an isolation and purification method for carotenoids from marigold flowers using a mixture of hexanes, absolute alcohol, and ethanolic potassium hydroxide. This patent uses numerous solvents that generate mixed solvent streams that are costly on a commercial scale to recover and separate. This patent does not employ a process that isolates zeaxanthin from a whole food source, nor does it describe certain process variables that are taught in the present invention.

Rodriguez, et al. (W.O. 01/94279 A2) provide a method for the purification of xanthophylls from marigold extracts that contain high levels of chlorophylls. This process teaches a method that uses various partitioning techniques with water, polar solvents, and nonpolar solvents to isolate lutein and zeaxanthin. These partitions are starting material dependant and are not needed in the current invention.

Thattaruparambil, et al. (W.O. 2004/018417) provide a method for isolating xanthophylls from marigold flowers and Chinese Wolf Berries that saponifies in an alcohol, extracts with ethyl acetate, washes with water, and purifies with a non-polar, polar, and alcohol solvent mixture. There are multiple solvents and steps in this process that are not needed in the present invention.

All patents cited in this application are herein incorporated by reference.

OBJECTS OF THE INVENTION

It is an object of the present invention to provide a method for saponifying and isolating xanthophyll esters. It is a further object of the present invention to provide an improved method of saponifying zeaxanthin esters. It is a further object of the present invention to provide a method of isolating zeaxanthin from an oleoresin wherein the oleoresin contains zeaxanthin esters. It is a further object of the present invention to provide a method of isolating zeaxanthin from a *Capsicum*-derived oleoresin in sufficient yield and of sufficient purity for use in medical, nutritional supplement or food additive applications.

BRIEF SUMMARY OF THE INVENTION

This invention relates to a practical and effective process of converting esterified xanthophylls, especially zeaxanthin, to non-esterified xanthophylls through saponification with minimal steps and handling. Other xanthophyll esters that can be saponified and isolated by this method include lutein esters, beta-cryptoxanthin esters, astaxanthin esters and the like. An embodiment involves hydrolysis of zeaxanthin esters contained in, for example, *Capsicum* plant source oleoresins by contacting said oleoresins with isopropyl alcohol, water, and an alkali for approximately 90 minutes (or until reaction completion) at a temperature of about 65° to 70° C. The saponified zeaxanthin is precipitated out using controlled, slow cooling to facilitate large crystal formation for ease of recovery. The solids are collected by centrifugation or filtration and washed with water, or a water/isopropyl alcohol mixture, until a desired purity level is obtained. Overall yields of zeaxanthin appear to be governed by the concentration of trans zeaxanthin and/or the percentage of owns zeaxanthin relative to the total amount of zeaxanthin in the starting material (see Examples 1 and 2). For example, a 2.68% zeaxanthin oleoresin input having 82% trans zeaxanthin to total zeaxanthin provides a 78% total zeaxanthin recovered yield of >98% trans zeaxanthin product, while a 14.4% zeaxanthin oleoresin input having 98% trans zeaxanthin provides a 91% total zeaxanthin recovered yield of >98% irons zeaxanthin product. Typically for this range of inputs, the esterified zeaxanthin in the first purified precipitate from the reaction has yields in the range of 60-95%, recoveries of the starting trans isomer >90%, and zeaxanthin purities >50%. Letting the cis zeaxanthin enriched supernatant solution stand over time allows the cis isomers to isomerize to the less-soluble trans isomer. As the zeaxanthin trans isomer builds up in concentration, the product precipitates out as it exceeds its solubility limit. Typically a minimum of about 10 days at room temperature is needed to achieve a good yield of this second precipitate (see Example 4). Longer time periods can be applied, but the incremental yield obtained may not be cost effective beyond a certain point. Alternatively higher temperatures may speed up this process, but the equilibrium point between the cis and trans isomers may shift as a function of temperature. One skilled in the art can optimize the time and isomer equilibrium point to be most commercially effective in terms of cost. It is also possible to warm the solution to dissolve the isomers once the desired amount of trans isomer is formed and slow cool it to achieve larger particle size zeaxanthin crystals for easier isolation. This additional yield can then be washed and dried to achieve a purity of >50% in the same manner as the initial yield.

DETAILED DESCRIPTION OF THE INVENTION

The present invention provides an economical and effective process for isolating, purifying, and recovering zeaxanthin in high yields, high purity and suitable for use in medical applications, nutritional supplement applications, food fortification applications, cosmetic applications and other applications. Zeaxanthin may be obtained from a variety of natural sources such as green vegetables, yellow/orange fruits and vegetables, various bacteria, from *Capsicum*-derived and other biomass, such as Chinese Wolfberries, using water and small amounts of benign solvents.

Sources

Zeaxanthin is commonly found in many fruits and vegetables, most notably Chinese wolfberries (Goji berries) of the genius *Lycium* and the fruits of paprika plants of the genus *Capsicum*. In much of the prior art, specific examples are given wherein lutein is isolated and/or purified from marigold oleoresin. Although they have many carotenoids and other phytochemicals in common, the chemical profile of marigold oleoresin and wolfberry oleoresin are different than that of *Capsicum* oleoresin (Khachik, U.S. Pat. No. 6,262,284). In an embodiment of the present invention, the fruit pods of orange paprika *Capsicum anmaan* which exhibit a hyperaccumulation of carotenoid pigment in the dried ripe fruit flesh, in which zeaxanthin is the dominant carotenoid, are used. (Todd, et al., U.S. Application Publication No. 2006/1085034, the disclosure of which is herein incorporated by reference in its entirety). The dried ripe fruit pod flesh of this *Capsicum* plant variety is extracted by means of solvent, supercritical fluid, or mechanical processing to provide an oleoresin consisting of resins and volatile oils that will be referred to herein as "oleoresin orange paprika." Chinese wolfberries, which also contain a preponderance of zeaxanthin in their carotenoid composition, are also a good source of raw materials for this process.

Saponification

Saponification includes the process of converting an organic ester into the corresponding alcohol and carboxylic acid soap by alkaline hydrolysis. Complete liberation of zeaxanthin esters to free or non-esterified form is helpful to effectively isolate and concentrate zeaxanthin to a desired extent. in the present invention, the oleoresin is completely dissolved in isopropyl alcohol to form a flowable, fluid solution that is easily mixed with water. The ratio of isopropyl alcohol and water to the amount of oleoresin can vary considerably and can be optimized by one skilled in the art. Generally speaking, one volume of starting oleoresin can be mixed with 1-3 volumes of isopropyl alcohol and 0.1-3 volumes of water to form a solution that is approximately 3-7 times the volume of the original starting material. The water, in part, serves to reduce the cost of the non-aqueous solvents by allowing the use of less non-aqueous solvent as well as to aid in the recovery of precipitated zeaxanthin. Zeaxanthin is not soluble in water but the soap by-products are, which allows them to be separated from the zeaxanthin. The isopropyl alcohol is added to assist in dissolving the starting oleoresin and to minimize the foaming issues during filtration that are created from soaps that are a by-product of the saponification process. The addition of isopropyl alcohol also lowers the viscosity of the reaction mixture, it aids in reducing saponification times, and improves filtration rates compared to an all aqueous approach (see Example 6). Isopropyl alcohol also aids in the purification of the zeaxanthin by solubilizing the other carotenoids (such as alpha-carotene, beta-carotene, etc.) without appreciably solubilizing the zeaxanthin. The degree of agitation and the temperature at which the reaction is performed can be varied considerably and optimized by simple experimentation by one skilled in the art. As one example, the mixture can be stirred and heated to 60-70° C. to ensure solubility of the oleoresin and to accelerate the saponification reaction. The concentration of the base used can be varied, as well. An aqueous, 45% potassium hydroxide solution, for example, can be added to the solution under constant agitation, although lower or higher base concentrations and even solid potassium hydroxide can be used. The required amount of alkali solution is approximately 0.5-1.5 times the amount of starting oleoresin (weight/weight) for the given 45% KOH concentration. The amount of base needed may be defined based on the starting amount of oleoresin, since both the oil and the xanthophylls need to be saponified, and not just the xanthophylls. The mixture can be maintained at the same temperature under nitrogen and with agitation for enough time for the saponification reaction to go to completion. Lower or higher temperature can also be used and optimized by one skilled in the art. Typically under 60-70° C. conditions, the reaction is complete in a time period of about 60 to 90 minutes. The status of the reaction can be monitored by thin layer chromatography, HPLC, or any other method commonly used in the art. Other alkali metal (Group 1a metals, for example, Li, Na) or alkaline earth metal (Group 2a metal, for example, Mg, Ca, Ba) hydroxides may be substituted for the preferred KOH.

Precipitation of Zeaxanthin

Zeaxanthin from natural sources is generally present in the form of the all-trans isomer. It is well documented that the trans isomer is less soluble than the cis isomers and is fairly easily precipitated into a solid at room temperature (Reilly, et al., U.S. application Ser. No. 12/800,416). The cis isomers do not form solids nearly as readily as the trans isomer and often are difficult to solidify at room temperature. An excellent review of cis-trans isomerization of carotenoids is given by Schieber, et al, 2005. Both the cis and the trans isomers have been detected in the human retina. From a production point of view, the trans isomers are more desirable because they are less soluble and crystallize out more readily from solutions making them easier to recover. Table 1 compares the solubility of trans zeaxanthin (Reilly, et al., U.S. application Ser. No. 12/800,416) and lutein (N. Craft et al., 1992). There are large solubility differences between lutein and zeaxanthin, and therefore, processes that work well for one of these xanthophylls may not work as well for the other. The solubility of zeaxanthin in isopropyl alcohol is about five times lower than that for lutein based on the data in Table 1. This does not take into account any matrix differences or the concentration of the carotenoid in that matrix. Examples 7 and 8 demonstrate how some of these differences manifest themselves when trying to apply the teachings of Madhavi, et al., U.S. Pat. No. 6,380,442 to zeaxanthin in *Capsicum* oleoresin extracts. Application of the teachings of Madhavi, et al., U.S. Pat. No. 6,380,442 resulted in poorer yields and incomplete reaction compared to the teachings of the instant invention (see Example 9).

TABLE 1

Solubility of trans zeaxanthin compared to lutein at room temperature.

| solvent | Zeaxanthin solubility (mg/L) | Lutein solubility (mg/L; Craft, 1992) |
| --- | --- | --- |
| THF | >20,355 | 8000 |
| DCM | 2956 | 800 |
| Acetone | 1631 | 800 |
| EtOAc | 1069 | 800 |
| MtBE | 726 | 2000 |
| MeOH | 82 | 200 |
| IPA | 81 | 400 |
| Hexane | 68 | 20 |
| EtOH | 40 | 300 |

Abbreviations used in Table 7 are THF=tetrahydrofuran, DCM=dichloromethane, EtOAc=ethyl acetate, MtBE=methyl tert-butyl ether, IPA=isopropyl alcohol or 2-propanol, EtOH=ethanol.

One of the most important teachings of the present invention deals with controlling conditions to affect the particle size of the precipitating zeaxanthin. During saponification, as the solution is heated, all the contents become soluble in the reaction mixture. At high temperature, the zeaxanthin remains soluble in the alcohol/water mixture until the reaction is complete. Once the reaction is complete, the mixture is allowed to cool slowly (Examples 3 and 9). The cooling rate, for example, less than or equal to 5° C. per hour, affects the particle size and thereby the ease by which the solid product can be isolated. A relatively large particle size zeaxanthin precipitates out during the slower cooling. Once the reaction reaches room temperature, additional all-trans zeaxanthin of relatively smaller particle size precipitates out of the solution over the next 72 hours. The two separate precipitation processes produce two separate distributions of particle size: a larger size distribution that crystallizes out with the slow cooling (generally >70 μm) and a smaller size distribution that precipitates after the reaction is at room temperature (generally ~10 μm). Typically, controlled, slow cooling at 5° C./hour provides an average crystal size between 70-85 microns. Crystal size >100 microns have also been observed using controlled, slower cooling techniques and could be optimized further for larger crystal size by those skilled in the art if needed. Any isolation difficulties caused by the difference in size can be alleviated by collecting and separating the larger particles, first, followed by heating the mixture to redissolve the smaller particles, and re-precipitation using slow cooling again (See Example 9).

Separation and Washing of Zeaxanthin Precipitate

Solid zeaxanthin, precipitated from the reaction mixture can be easily separated from the reaction mixture by filtration, decantation, centrifugation, or any other separation technique known to those who are skilled in the art. Filtration is a typical embodiment. Filtering allows the reaction mixture to be recirculated until a filter cake is formed, with the larger crystals acting as a filter aide to trap and aid in the recovery of the smaller particles. Once the filter cake is collected it can be washed with water, isopropyl alcohol, or a water/isopropyl alcohol mixture until the desired purity is reached. Although the ratio of water to isopropyl alcohol may be varied in practice, rinsing the cake with a volume of 50:50 water:isopropyl alcohol equal to one-third the volume of the initial reaction mixture generates a product reaching a purity of >50%. The precipitate wash can be mixed with the collected precipitate and filtered again, or simply run through the original filter cake to wash away excess soaps and other water soluble "impurities". A zeaxanthin purity >90% can be achieved with sufficient precipitate washing. The addition of an alcohol (such as isopropyl alcohol) appears to increase the wash efficiency by dissolving impurities, such as carotenes, that are not soluble in water. See Example 5 for washing details. Note that Example 5 was a washing study done to show the difference in wash effectiveness between water and a water/isopropyl alcohol mixture. Example 9 demonstrates the purities and yields possible when these conditions are implemented.

Drying and Marketable Carrier

Once the zeaxanthin has been isolated and washed to a desired purity level, it can be treated using a variety of methods available to those who are skilled in the art to remove residual solvents and water. Careful consideration should be used in the drying process to minimize the conditions that can lead to degradation of the product. Once a dry zeaxanthin product is obtained it can be used as is or converted to a micro-encapsulated form. Such a form may be suited for nutritional supplement, beverage or cosmetic uses, and can provide an oxygen barrier that increases the stability of the product.

Additional Collection of Yield

The initial recovered yield of zeaxanthin is directly correlated to the amount of trans zeaxanthin in the starting material; the higher the percentage trans zeaxanthin to total zeaxanthin (combination of trans and cis isomers) in the starting material the higher initial collected yield is expected. The present invention also increases the trans isomer relative to cis isomers in the final zeaxanthin product and also increases purity. This is due to the fact that the trans isomer is less soluble, as previously mentioned, thus making it easier to isolate, leaving behind the soluble cis isomers. Any conversion of the cis isomers to trans would improve total zeaxanthin recovery.

There has been some work that shows refluxing cis isomers at low temperatures (~65° C.) to initiate isomerization to trans isomers in the presence of a hydrocarbon and alcohol (Reilly, et al., U.S. application Ser. No. 12/800,416) with some success. This approach increased the total zeaxanthin yield by as much as 15% but this approach does not work in the present mixture of isopropyl alcohol and water due to the combination of high temperatures needed to bring the reaction to reflux (approximately 100° C.) and strong basic conditions. At these higher temperatures and strong basic conditions, the reverse affect of degradation of trans isomers to cis isomers occurs similar to the teachings of Reilly, et al. U.S. application Ser. No. 12/800,416, so elevated temperatures (>90° C.) in this reaction combination and pH should be avoided.

The conversion of cis zeaxanthin to trans zeaxanthin in the supernatant at room temperature over time has been observed (see Example 4 and Example 9). It is recommended to let the conversion happen for at least about 10 days at room temperature. Higher temperatures may accelerate the conversion, but may change the equilibrium point between the concentrations of cis and trans isomers. The teachings of Reilly, et al. U.S. application Ser. No. 12/800,416 would indicate that heating at 65° C. would be beneficial in terms of cis to trans isomer conversion. Those skilled in the art can optimize the balance between time, % conversion and ultimate cost-effectiveness of the conversion process.

This trans zeaxanthin in the supernatant can be collected and washed in the same manner as described previously. For example, a 2.68% zeaxanthin oleoresin input having 82% trans zeaxanthin provided a 76% total zeaxanthin recovered yield of >98% trans isomer ratio and >60% zeaxanthin purity product in the initial yield. The cis isomer enriched filtrate from the initial separation was allowed to sit and convert to the desirable trans isomer which was collected in a second filtration to yield an additional 15% total zeaxanthin yield of >98% trans isomer ratio and >60% zeaxanthin purity for a combined total of 91% total zeaxanthin recovered yield of >98% trans zeaxanthin and >60% zeaxanthin purity (see Example 9).

The data in Example 4 shows that the % trans zeaxanthin increased over time as the % cis zeaxanthin decreases, all while the % total zeaxanthin remains relatively constant. This indicates that zeaxanthin is stable to degradation under these conditions, but that the cis isomer converted to the more desirable trans isomer, which also resulted in an increased isolated yield. Including. this secondary recovery process brings important economic benefits by increasing the overall yield, particularly for starting materials that contain higher initial cis to total isomer ratios.

EXAMPLES

The subject matter of the instant invention will be better understood in connection with the following examples, which are intended as an illustration of and not a limitation upon the scope of the invention.

Example 1

An orange paprika extract (oleoresin) containing 2.68% total zeaxanthin (40.36 g) was placed in a 500 mL 3-necked, round bottom flask equipped with an overhead stirrer, heating mantle, nitrogen inlet and outlet, and thermometer. Isopropyl alcohol (60.07 g), water (reverse osmosis-grade, 60.06 g) and potassium hydroxide solution (45%, aqueous, 30.03 g) was added. The reaction was stirred and heated under nitrogen until the reaction reached 65° C. The temperature was maintained for 90 minutes and complete saponification was confirmed by thin layer chromatography. The heat and stirring was turned off while keeping the round bottom flask in the heating mantle to assist in slow cooling to promote larger crystal growth. The reaction was allowed to stand for 72 hours to allow crystallization to occur. The mixture was then filtered through fluted filter paper. The precipitate was collected and mixed with agitation with 100 mL reverse osmosis-Ode water for 30 minutes. This wash/precipitate mixture was then re-filtered through a clean piece of fluted filter paper. The washed precipitate was collected and dried overnight in a vacuum oven at 40° C. and analyzed for zeaxanthin. A table of the results is given below:

TABLE 2

Results for zeaxanthin (Zea) for the experiment described in Example 1.

|  |  |  |  |  | Purity of Zeaxanthin | | | Isomer Fraction | |
|---|---|---|---|---|---|---|---|---|---|
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 40.36 | 0.888 | 0.191 | 1.080 | 2.20 | 0.47 | 2.68 | 82.28% | 17.72% |
| Recovered Precipitate | 1.33 | 0.833 | 0.007 | 0.839 | 62.61 | 0.49 | 63.10 | 99.23% | 0.77% |
| % Yield of Recovered Zea in Precipitate vs. Starting Material |  | 93.74% | 3.40% | 77.73% |  |  |  |  |  |

Example 2

The process described in Example 1 was repeated using a starting material that was higher in both trans/total zeaxanthin ratio as well as total zeaxanthin concentration. Results are given in the Table 3.

TABLE 3

Results zeaxanthin (Zea) for the experiment described in Example 2.

|  |  |  |  |  | Purity of Zeaxanthin | | | Isomer Fraction | |
|---|---|---|---|---|---|---|---|---|---|
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 44.08 | 6.216 | 0.130 | 6.346 | 14.10 | 0.29 | 14.40 | 97.96% | 2.04% |
| Recovered Precipitate | 15.79 | 5.647 | 0.100 | 5.747 | 35.76 | 0.64 | 36.40 | 98.25% | 1.75% |
| % Yield of Recovered Zea in Precipitate vs. Starting Material |  | 90.84% | 77.49% | 90.57% |  |  |  |  |  |

The recovered precipitate in this example was not dried prior to HPLC analysis. It contained 44.13% solvent (water and IPA). Adjusting for the solvent and water and then calculating purity on a dry weight basis would have brought the % total zeaxanthin purity up to 65.15%, which is consistent with the recovered total zeaxanthin purity reported on a dry weight basis in Example 1. This experiment was only done to show the collected yields are dependant on the amount of trans zeaxanthin is in the starting material. Examples one and two give clear evidence that the total yield of free, non-esterified zeaxanthin is dependent on the amount of trans zeaxanthin is in the starting material.

Example 3

Particle size plays a vital role in filtration efficiency, with larger particle size providing easier recovery. The particle size of the precipitating zeaxanthin crystal can be controlled by controlling a number of variables, with the easiest being temperature and time. A set of three experiments were run simultaneously to demonstrate the effect of temperature and time on the particle size of the precipitating zeaxanthin. Controlled, slow cooling provided larger particle sizes.

TABLE 4

Experimental settings and results for Example 3.

| Experiment | A | B | C |
|---|---|---|---|
| Starting oleoresin (g) | 40.01 | 40.02 | 40.00 |
| Isopropyl alcohol (g) | 121.80 | 122.85 | 120.96 |
| 45% aqueous potassium hydroxide (g) | 29.99 | 30.05 | 30.04 |
| Temperature of reaction (° C.) | 60 | 60 | 60 |
| Reaction time (minutes) | 90 | 90 | 90 |
| Precipitation conditions | 0° C. overnight | Room temperature overnight | Slow cool (5° C./hour) to room temp. |
| Average crystal size (micron) | 24.14 | 28.27 | 71.04 |

Results for experiment C coincide with the typical 70-85 micron crystal size that is obtained with controlled, slow cooling at 5° C./hour

Example 4

Figure 2:
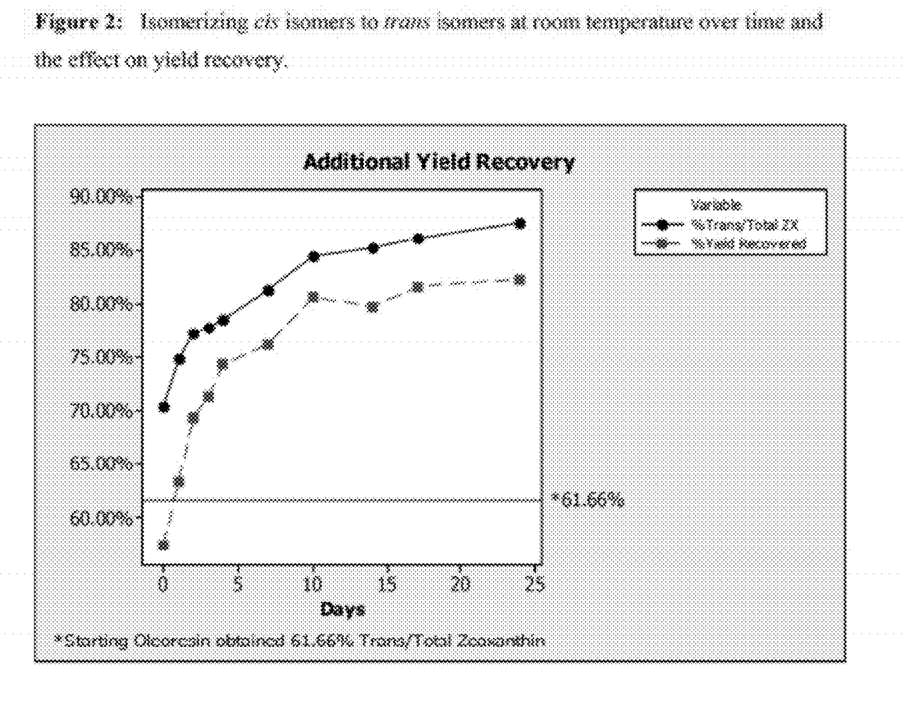
FIG. 2. Isomerizing cis isomers to trans isomers at room temperature over time and the effect on yield recovery.

Additional yield can be isolated from a mixture that contains a combination of trans and cis isomers, by allowing the mixed isomer solution to sit at room temperature for a period of time. The additional yield is attributed to the conversion of the very soluble cis isomers to the less soluble trans isomer, which begins to precipitate out of solution as it exceeds its solubility limit. A paprika extract (oleoresin) containing 2.75% total zeaxanthin (600.05 g) was placed in a 3-necked, round bottom flask equipped with an overhead stirrer, heating mantle, nitrogen inlet and outlet, and thermometer. Isopropyl alcohol (1800.30 g), and potassium hydroxide solution (45%, aqueous, 450 g) was added. The reaction was stirred and heated under nitrogen at 60° C. for 90 minutes. The reaction was treated with a volume of reverse osmosis-grade water equal to the volume of the reaction mixture and was then allowed to cool and was analyzed for zeaxanthin and isomer ratios by HPLC over a period of 24 days (see "reaction mixture" in Table 5). For each time interval, the mixture was stirred to insure homogeneity before a portion was removed and filtered through fluted paper to test recovery yields (filtrate and precipitate were both assayed for zeaxanthin content and % yields were calculated from the results). Results are shown in the graph in FIG. 2.

TABLE 5

Weights and HPLC results from experiment described in Example 4.

| SAMPLE | Days | Input MASS (g) | wt % total Zea | wt % trans Zea | wt % cis Zea | % trans/ Total ZX | % Total Zea Recovered Yield |
|---|---|---|---|---|---|---|---|
| Starting Oleoresion | | 600.05 | 2.75 | 1.70 | 1.06 | | |
| Reaction Mixture | 0 | 281.66 | 0.30 | 0.21 | 0.09 | 70.47% | 57.36% |
| | 1 | 280.12 | 0.29 | 0.22 | 0.07 | 74.91% | 63.36% |
| | 2 | 354.09 | 0.19 | 0.15 | 0.04 | 77.32% | 69.36% |
| | 3 | 294.97 | 0.24 | 0.19 | 0.05 | 77.78% | 71.39% |
| | 4 | 282.5 | 0.29 | 0.23 | 0.06 | 78.55% | 74.33% |
| | 7 | 270.8 | 0.29 | 0.23 | 0.05 | 81.40% | 76.28% |
| | 10 | 284.48 | 0.30 | 0.26 | 0.05 | 84.49% | 80.71% |
| | 14 | 271.12 | 0.29 | 0.25 | 0.04 | 85.37% | 79.85% |
| | 17 | 292.54 | 0.31 | 0.26 | 0.04 | 86.27% | 81.67% |
| | 24 | 295.64 | 0.29 | 0.26 | 0.04 | 87.76% | 82.36% |

This technique, to obtain additional yield by allowing the cis isomers to isomerize to trans isomers, can carried out in a number of ways. One method, described in this example, allows the reaction mixture to sit at room temperature until the desired trans isomer ratio is obtained before isolation. A similar result can be achieved in a two-stage isolation process. Here, after initial isolation of zeaxanthin by filtration or centrifugation, the cis isomer rich filtrate or supernatant is allowed to sit until the desired trans ratio is obtained. The second crop of product is obtained by a second filtration or centrifugation step. This process can be repeated until the desired yield is obtained. It should be kept in mind, however, that additional wash steps may be necessary to reach a desired purity level in the collected precipitate, whether using a single or multiple isolation steps. One skilled in the art can optimize the protocol for the size and number of wash steps as a function of the recovery of the zeaxanthin from any subsequent filtration steps.

Example 5

A side by side experiment was done to determine the effectiveness of a water wash versus a water/isopropyl alcohol mixture wash on purity and yield. Less than optimal amounts of the wash solutions were applied in equal volumes in an attempt to accentuate the washing efficiency difference between water and a 50:50 (vol/vol) water/isopropyl alcohol mixture. Therefore optimal purities were not achieved in this experiment. The protocol in Example 9 uses more optimal volumes. Both experiments were run under the same conditions and filtered through fluted paper to obtain two separate initial precipitates. These precipitates were left on the fluted paper and in one case, the precipitate was treated with 100 mL of reverse osmosis-grade water. The other precipitate was treated with 100 mL of a 50:50 mixture (reverse osmosis-grade water:isopropyl alcohol). A smaller amount of wash was applied, than in the optimal case (Example 9), to these experiments to show wash efficiency without reaching a purity maximum. The results are shown in the Table 6. The % total zeaxanthin in the final dry precipitate was higher with the 50:50 isopropyl alcohol:water wash. It is also interesting to note that the two experiments differ in the yield of the final precipitate, but most of that difference can be traced to what did not precipitate out of the filtrate. This has nothing to do with the washing procedure or wash solvents, since that occurred after the precipitation. The loss of yield to the wash filtrates was about 1% greater for the 50:50 isopropyl alcohol:water wash than the water wash filtrate. This indicates that both washes produce very similar yields from the washing step, but that the 50:50 isopropyl alcohol:water wash is more efficient in removing impurities. Those skilled in the art could use this information to further optimize the wash volumes to minimize solvent usage and yield loss to obtain necessary purity targets.

TABLE 6

Experimental results to show affects on yield and purity of zeaxanthin (Zea) between a (a) 100% water wash and a (b) 50:50 (water:isopropyl alcohol) wash.

| | | Purity of Zeaxanthin | | | |
|---|---|---|---|---|---|
| Sample | Amount (g) | % trans Zea | % cis Zea | % total Zea | % Total Zea Yield |
| (a) 100% Water Wash | | | | | |
| Starting Material | 40.08 | 2.20% | 0.47% | 2.68% | 100.00% |
| Initial Filtrate | 165.00 | 0.09% | 0.08% | 0.18% | 27.09% |
| Wash Filtrate | 101.13 | 0.01% | 0.01% | 0.02% | 2.26% |
| Final Dry Recovered Precipitate | 5.54 | 13.40% | 0.21% | 13.62% | 70.37% |
| Total | | | | | 99.72% |
| (b) 50:50 (Water:IPA) Wash | | | | | |
| Starting Material | 40.15 | 2.20% | 0.47% | 2.68% | 100.00% |
| Initial Filtrate | 165.28 | 0.10% | 0.12% | 0.22% | 33.70% |
| Wash Filtrate | 92.17 | 0.02% | 0.02% | 0.04% | 3.26% |
| Final Dry Recovered Precipitate | 2.37 | 27.96% | 0.57% | 28.53% | 62.96% |
| Total | | | | | 99.92% |

Example 6

A side by side experiment was performed to show the impact isopropyl alcohol has on the efficiency of zeaxanthin isolation. The experiments were run following the method described in Example 1 (Example A using 40.26 g of oleoresin orange paprika and Example B using 40.51 g) with the exception of water replacing the addition of isopropyl alcohol in Experiment A. Both experiments were held at 65° C. for 90 minutes for saponification to take place and filtered after sitting for 72 hours at ambient temperature. The viscosity of Experiment A (water only) was higher viscosity, having the consistency of used motor oil, compared to Experiment B (water and IPA) which was very fluid and had the consistency of water. The experiments were filtered with vacuum through a WHATMAN®, Schleicher & Schuell, 55 mm paper filter disk on a Buchner funnel into an Erlenmeyer flask. Neither resulting precipitates were washed in order to emphasize the difference in recovery efficiency; however, washing the recovered precipitate using the techniques previously described will result in adequate purities. Results are shown in Table 7.

alcohol (approximately 120 mL) at 65° C., forming a free-flowing solution. An aqueous 50% potassium hydroxide solution (prepared by combining 3.6 grams of solid potassium hydroxide and 3.6 grams of reverse osmosis-grade water) was added to the mixture. The temperature was maintained for 90 minutes and allowed to cool to room temperature. The reaction mixture was then mixed with water (approximately 170 mL reverse osmosis-grade) to reduce the solvent concentration to approximately 50% (volume/volume), stirred, and allowed to stand at room temperature for 4 hours. After 4 hours the reaction was sampled and analyzed by HPLC which showed that only 53% of the zeaxanthin esters were saponified. The reaction mixture was then mixed with 1,360 mL of reverse osmosis-grade water and stirred. The resulting mixture was then centrifuged in 250 mL bottles for 30 minutes at 1,900 rpm on an IEC model K centrifuge. Most of the precipitate sank to the bottom of the centrifuge bottle but there was still a noticeable amount of precipitate visible in the supernatant layer. This was most likely due to the specific

TABLE 7

Results for zeaxanthin (Zea) from Example 6 showing the benefits of the addition of isopropyl alcohol (IPA).

| Sample | Recovered Amount (g) | Solvent Used | % trans Zea | % cis Zea | % total Zea | % total Zea yield | % trans Zea Yield | Filter Time | % Zea Saponified |
|---|---|---|---|---|---|---|---|---|---|
| Starting Material | | | 2.11% | 0.50% | 2.61% | 100.00% | 100.00% | | |
| Ex. A Dry Precipitate | 52.17 | Water only | 0.46% | 0.11% | 0.57% | 28.12% | 28.28% | 2.25 hours | 50.68% |
| Ex. B Dry Precipitate | 10.31 | Water & IPA | 7.65% | 0.77% | 8.42% | 82.18% | 92.37% | 18 minutes | 99.98% |

*Note: Experiment B filter paper completely blinded after 2.25 hours leaving thick paste on filter paper.

The results show that isopropyl alcohol decreases the amount of time necessary for saponification and increases filtration rates by decreasing the viscosity. While Experiment B was completely saponified in about 90 minutes, Experiment A was only about ½ complete. Experiment A also experienced foaming issues in both the reaction and in filtering that were not seen with isopropyl alcohol in Experiment B.

Example 7

An experiment was performed that followed the protocol described in Madhavi, et al., U.S. Pat. No. 6,380,442 which shows that the teachings of the present invention are needed to produce a quality product with high yields. Oleoresin orange paprika (40.09 g) containing 2.68% zeaxanthin and 4.5% total carotenoids was dissolved in 3 volumes of isopropyl gravity of the mixture and size of the particles. To ensure maximum collection of precipitate, the mixture was then stirred and filtered using the filter procedure described in Example 6. The resulting filtrate was free of visible precipitate. The filtered precipitate was washed twice with 100 mL water, filtered through clean filter paper after each wash, and dried in a vacuum oven at room temperature. The results are shown in Table 8. Note that in Example 1, the initial precipitate was also washed only with water to give a product with >60% purity.

TABLE 8

Results for zeaxanthin (Zea) for the experiment described in Experiment 7.

| | | | | | Purity of Zeaxanthin | | | Isomer Fraction | |
|---|---|---|---|---|---|---|---|---|---|
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 40.09 | 0.882 | 0.190 | 1.072 | 2.20 | 0.47 | 2.68 | 82.28% | 17.72% |
| Recovered Precipitate | 0.64 | 0.327 | 0.001 | 0.328 | 51.12 | 0.19 | 51.31 | 99.63% | 0.37% |
| % Yield of Recovered Zea in Precipitate vs. Starting Material | | 37.08% | 0.63% | 30.62% | | | | | |

The method described in Madhavi, et al., U.S. Pat. No. 6,380,442 results in product with >50% purity, but at the cost of very low and un-economical yields. This experiment was repeated in Example 8 using more alkali to allow the reaction to reach completion in the given amount of time.

Example 8

An experiment was performed that followed the protocol described in Madhavi, ei al., U.S. Pat. No. 6,380,442 using the amount of alkali provided in the present invention to show that increased base alone is not sufficient, but that the additional teachings in the present invention are also required to produce a quality product with high yields. Oleoresin orange paprika containing 2.68% total zeaxanthin (40.08 g) was dissolved in 3 volumes of isopropyl alcohol (approximately 120 mL) at 65° C. to form a free-flowing solution. Aqueous 45% potassium hydroxide solution (30.11 g) was added to the mixture. This is approximately 0.75 times the amount of starting oleoresin. The temperature was maintained at 65° C. for 90 minutes and then allowed to cool to room temperature. The mixture was then diluted with a 50% (volume/volume) amount of water (approximately 190 mL reverse osmosis-grade) and allowed to sit at room temperature for 4 hours. After 4 hours the reaction was tested by HPLC to show that 99.97% of the zeaxanthin esters were saponified. The reaction mixture was then diluted with 1,520 mL reverse osmosis-grade water. The resulting mixture was then centrifuged in 250 mL bottles for 30 minutes at 1,900 rpm on an IEC model K centrifuge. Due to the specific gravity of the mixture and size of the particles the particles remained suspended after centrifuging with little to no precipitate being centrifuged out. The mixture was then mixed and filtered following the filter procedure described in Example 6. The filtered precipitate was washed twice with 100 mL water, filtered through clean filter paper after each wash, and dried in a vacuum oven at room temperature. The results are shown in Table 9.

utes in the initial filtration for this experiment compared to the 18 minutes shown in Example 6 using the present invention. Smaller particles tend to plug filter media faster than larger particles resulting in longer filtration times. The crystal size of zeaxanthin was measured for this example and the mean size was 26 microns compared to the typical average of 70-80 microns size produced in the present invention.

Example 9

An experiment was performed to show an example of optimal results for the teachings described in the present invention. A paprika extract (oleoresin) containing f2.68% total zeaxanthin (40.22 g) was placed in a 500 mL 3-necked, round bottom flask equipped with an overhead stirrer, warm water bath, nitrogen inlet and outlet, and thermometer. Isopropyl alcohol (60.33 g), water (reverse osmosis-grade, 60.17 g) and potassium hydroxide solution (45%, aqueous, 30.10 g) was added. The reaction was stirred and heated under nitrogen until the reaction reached 65° C. The temperature was maintained for 90 minutes and complete saponification was confirmed by thin layer chromatography. The stirring was turned off and the water bath was cooled at a rate of 5° C./hour to assist in slow cooling to promote larger zeaxanthin crystal growth. The average particle size typically ranges from 70-85 microns, but particle sizes greater than 100 microns have been observed using this controlled, slow cooling technique. The reaction was allowed to stand for 72 hours to allow further crystallization to occur. The mixture was then filtered through fluted filter paper. 168.82 g of filtrate was collected and set aside for future work. The collected precipitate was trans-

TABLE 9

Results for zeaxanthin (Zea) for the experiment described in Experiment 8.

| | | | | | Purity of Zeaxanthin | | | Isomer Fraction | |
| --- | --- | --- | --- | --- | --- | --- | --- | --- | --- |
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 40.08 | 0.882 | 0.190 | 1.072 | 2.20 | 0.47 | 2.68 | 82.28% | 17.72% |
| Recovered Precipitate | 0.91 | 0.497 | 0.001 | 0.499 | 54.67 | 0.12 | 54.79 | 99.79% | 0.21% |
| % Yield of Recovered Zea in Precipitate vs. Starting Material | | 56.40% | 0.55% | 46.50% | | | | | |

The results show that the method described in Madhavi, et al., U.S. Pat. No. 6,380,442 results in >50% purity, but extremely low yields that are much lower than the yields described for the present invention as illustrated in Example 9. The product from this example required significantly more time to filter compared to the product prepared by the method described in the present invention. Filtering required 36 minferred to a beaker with a stir bar and mixed with 50:50 water (reverse osmosis-grade):IPA mixture (64.97 g) for 15 minutes. The solution was filtered again through a clean piece of fluted filter paper. The collected precipitate was dried at room temperature in a vacuum oven. The dried precipitate was analyzed by HPLC (61.54% purity) and the results are shown in Table 10.

TABLE 10

Results for zeaxanthin (Zea) from the initial recovery described in Example 9.

| | | | | | Purity of Zeaxanthin | | | Isomer Fraction | |
| --- | --- | --- | --- | --- | --- | --- | --- | --- | --- |
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 40.22 | 0.885 | 0.191 | 1.076 | 2.20 | 0.47 | 2.68 | 82.28% | 17.72% |
| Recovered Precipitate | 1.33 | 0.816 | 0.003 | 0.818 | 61.34 | 0.20 | 61.54 | 99.68% | 0.32% |

TABLE 10-continued

Results for zeaxanthin (Zea) from the initial recovery described in Example 9.

| | | | | | Purity of Zeaxanthin | | | Isomer Fraction | |
|---|---|---|---|---|---|---|---|---|---|
| Sample | Mass (g) | g Trans Zea | g Cis Zea | g Total Zea | % Trans Zea | % Cis Zea | % Total Zea | % Trans in Total Zea | % Cis in Total Zea |
| % Yield of Recovered Zea in Precipitate vs. Starting Material | | 92.16% | 1.39% | 76.07% | | | | | |

The initial 168.82 g of filtrate was analyzed for zeaxanthin by HPLC and allowed to sit at room temperature for 14 days to allow the conversion of cis isomers to the more desirable trans isomers. After 14 days the filtrate was heated to 65° C. in a warm water bath for 90 minutes and slow cooled 5°/hour in the same manner as the saponification to promote large crystal growth. Once the mixture reached room temperature the mixture was allowed to sit for 72 hours and filtered again through fluted filter paper. The collected precipitate was washed with 65.03 g of a 50:50 water (reverse osmosis-grade):IPA in a beaker in the same manner as previously described. The solution was filtered through a clean fluted filter paper, dried at room temperature in a vacuum oven, and analyzed by HPLC. The results for the additional collected precipitate (60.32% purity) are shown in Table 11.

TABLE 11

Results for zeaxanthin (Zea) from the additional collected precipitate described in Example 9.

| | | | | | Purity of Zeaxanthin | | | Isomer Fraction | |
|---|---|---|---|---|---|---|---|---|---|
| Sample | Mass (g) | g Trans Zea | g Cis Zea | g Total Zea | % Trans Zea | % Cis Zea | % Total Zea | % Trans in Total Zea | % Cis in Total Zea |
| Starting Material | 40.22 | 0.885 | 0.191 | 1.076 | 2.20 | 0.47 | 2.68 | 82.28% | 17.72% |
| Initial Filtrate* | 168.82 | 0.078 | 0.187 | 0.265 | 0.05 | 0.11 | 0.16 | 29.30% | 70.70% |
| Recovered Precipitate | 0.27 | 0.162 | 0.001 | 0.163 | 60.11 | 0.21 | 60.32 | 99.65% | 0.35% |
| % Yield of Recovered Zea in Precipitate vs. Initial Filtrate | | 208.99% | 0.30% | 61.46% | | | | | |
| % Yield of Recovered Zea in Precipitate vs. Starting Material | | 18.33% | 0.30% | 15.14% | | | | | |

*Initial Filtrate was analyzed by HPLC right after the initial filtration. The filtrate then sat for 14 days prior to being filtered for additional recovered yield to allow cis zeaxanthin to convert to trans zeaxanthin.

The additional collection of precipitate was combined with the initial precipitate to give a 91.21% total zeaxanthin yield from the starting oleoresin. The precipitate from the initial recovery and additional recovery both had purities >60% total zeaxanthin. The combined collected precipitate also resulted in 110.49% of the total trans zeaxanthin yield from the starting material which indicates the isomerization of cis zeaxanthin to the trans zeaxanthin isomer. This is also evident from Table 11 since the initial filtrate contained 0.078 g of the trans zeaxanthin isomer and 0.187 g of the cis zeaxanthin isomer, while the recovered solid from that filtrate contained 0.162 g of the trans zeaxanthin isomer and 0.001 g of the cis zeaxanthin isomer.

Example 10

Goji berry extract is saponified using the method described in Example 9. The resulting reaction mixture is filtered to obtain greater than 90% of the starting trans zeaxanthin and is washed and is dried to obtain greater than 50% zeaxanthin product.

Example 11

Marigold extract containing the xanthophylls lutein and/or zeaxanthin is saponified using the method described in Example 9. The resulting reaction mixture is filtered to obtain greater than 90% of the starting trans xanthophylls and is washed and is dried to obtain greater than 50% total xanthophyll product.

REFERENCES

1. Ausich, Rodney L.; David J. Sanders, International Application Publication No. WO 97/23436 A1, Published Jul. 3, 1997.
2. Chopra M., Thurnham D I, "Effect of Lutein on oxidation of low density lipoproteins (LDL) in vitro," Proceedings of the Nutrition Society, 1994; 53: 1993 #18A.
3. Ernst, Hansgeorg; Henrich Klaus, Ditrich Klaus, U.S. Pat. No. 6,747,177.
4. Ferrater, Martorell Joan Caries; Fernandez, Martin Juan Antonio; Ribera, Ruiz David; Viso, Acosta Antonio, Spanish Pat. No. ES 2,265,787 A1, Published Feb. 16, 2007.
5. Howard A N, Williams N R, Palmer C R, Cambou J P, Evans A E, Foote J W, et al., "Do hydroxyl-carotenoids prevent coronary heart disease?", International Journal of Vitamin and Nutrition Research, 1996; 16; 3689-3694.

6. Howard, Allan Norman; John T. Landrum, Richard A. Bone, U.S. Pat. No. 6,329,432.
7. Khachik et al., Isolation and structure elucidation of geometric isomers of lutein, zeaxanthin in extracts of human plasma, J. Chrom. 582, 153-156, 1992.
8. Khachik, Fredrick; U.S. Pat. No. 6,262,284.
9. Madhavi, Doddabele L.; Daniel I. Kagan, U.S. Pat. No. 6,380,442.
10. Muralidhara, Harapanagalli S.; Tracy Lee Cornuelle, U.S. Pat. No. 5,847,238.
11. N. Craft et al., Journal of Agricultural Food Chemistry (1992) 40, 431-434.
12. Quesnel Yannick; European Patent Application EP 1,371,641 A1, Published Dec. 17, 2003.
13. Quesnel, Yannick; International Application Publication No. WO 03/104190 A1, Published Dec. 18, 2003.
14. Quesnel, Yannick; U.S. Application Publication No. U.S. 2005/1039145, Published Jun. 30, 2005.
15. Reilly, Mark; Josh James Tuinstra, Lucas Chadwick, Mark Porter, James Barren, Gregory Reynhout, U.S. Provisional Application Ser. No. 60/994,801.
16. Roberts, Richard L.; Justin Green, Brandon Lewis, *Clinics in Dermatology,* (2009) 27, 195-201.
17. Rodriguez, Gustavo; Mario-David Torres-Cardona, Alejandro Diaz, International Application Publication No. WO 01/94279 A2, Published Dec. 13, 2001.
18. Sanz, Ridaura; Vicente Ernesto, Garcia Correa, Oscar Ruben, Prado Naranjo, Armando, International Application Publication No. WO 99/23067, Published May 14, 1999.
19. Schieber, Andreas; Reinhold Carle, Trends in Food Science and Technology (2005) 16, 416-422.
20. Seddon, J. M. et al., 1994, Dietary Carotenoids, Vitamins A, C, and E, and Advanced Age-Related Macular Degeneration," J. Am. Med. Assoc. 272(9), pp. 1413-1420.
21. Swaminathan, Sethuraman; Kunhiraman Priya Madavalappil, International Application Publication No. WO 2006/114794 A1, Published Nov. 2, 2006.
22. Thattaruparambil Krishna Das, Sunil, Kumar; Sherena Padintaravattom, Abdul, Kadir; Sajoy, Sebastin; International Application Publication No. WO 2004/018417, Published Apr. 3, 2004.
23. Todd, Paul H.; Carrie K. Young, Carol L. Locey, James P. Barren, Anthony P. Vandenhombergh, Donald R. Berdahl, Jeffrey S. Kanel, U.S. Application Publication No. US 2006/1085034, Published Aug. 17, 2006.
24. Xu, Shuiming; Fengming Shen, Chinese Pat. No. CN 1,436,774A, Published Feb. 2, 2002.

The invention claimed is:

1. A method for isolating xanthophylls from a xanthophyll ester source, comprising the steps of:
(a) dissolving or suspending the xanthophyll ester source in isopropyl alcohol and water at a temperature of about 40-90° C. to form a free-flowing mixture;
(b) hydrolyzing the mixture from step (a) with an aqueous saponifying agent;
(c) cooling the saponified mixture at a rate of about at about 2-15° C. hour to about ambient temperature and allowing the mixture to sit for at least 5 hours to 24 days;
(d) recovering precipitated xanthophylls;
(e) optionally, washing the precipitated xanthophylls until a desired purity level is reached;
(f) optionally, drying the precipitated xanthophylls from step (d) or step (e) to eliminate residual solvent and water;
(g) optionally, allowing residual liquid from which the precipitated xanthophylls have been removed in step (d) to stand for at least 1 day to 24 days to form additional precipitated xanthophylls and recovering the additional precipitated xanthophylls; and
(h) optionally, reheating the additional precipitated xanthophylis from step (g) to 40-90° C. in a solvent, then repeating steps (c)-(f), and recovering the precipitated xanthophylls.

2. The method of claim 1, wherein steps (g)-(h) are repeated to obtain additional precipitated xanthophylls.

3. The method of claim 1, wherein the xanthophyll ester is selected from zeaxanthin, lutein, beta-cryptoxanthin, astaxanthin, capsanth in, capsorubin, and mixtures thereof.

4. The method of claim 1, wherein the xanthophyll ester is zeaxanthin.

5. The method of claim 1, wherein the xanthophyll ester is lutein.

6. The method of claim 1, wherein the xanthophyll ester source is selected from fruits of paprika plants of the genus *Capsicum*, Goji berries of the genus *Lycium* and marigolds of the genus *Tagetes.*

7. The method of claim 1, wherein the xanthophyll ester source is an extract from the fruits of paprika plants of the genius *Capsicum.*

8. The method of claim 1, wherein the weight to weight ratio of xanthophyll ester source to isopropyl alcohol solvent in step (a) ranges from about 1 to 3.

9. The method of claim 1, wherein the weight to weight ratio of xanthophyll ester source to water in step (a) ranges from about 0.1 to 3.

10. The method of claim 1, wherein the temperature in step (a) and step (h) ranges from about 60-70° C.

11. The method of claim 1, wherein the aqueous saponifying agent in step (b) is 45% KOH and the weight to weight ratio of 45% KOH to xanthophyll ester source ranges from 0.5 to 1.5.

12. The method of claim 1, wherein the aqueous saponifying agent in step (b) comprises an alkali metal, or an alkaline earth metal hydroxide or oxide.

13. The method of claim 12, wherein the aqueous saponifying agent comprises potassium hydroxide.

14. The method of claim 13, wherein the temperature in step (b) is maintained at about 40-90° C. until complete saponification is achieved.

15. The method of claim 1, wherein the temperature in step (b) is maintained at about 40-90"C for about 90 minutes.

16. The method of claim 1, wherein the saponified solution in step (c) is allowed to sit for about 72 hours.

17. The method of claim 1, wherein the saponified solution in step (c) is allowed to sit for greater than 72 hours to 24 days.

18. The method of claim 1, wherein the xanthophylls of step (d), step (g) and/or step (h) are additionally washed and followed by a precipitate isolation technique until desired purity is reached.

19. The method of claim 1, wherein the precipitated xanthophylls are washed in step (e) with an aqueous solution, a solvent or an aqueous/solvent mixture.

20. The method of claim 19, wherein the solvent is an alcohol.

21. The method of claim 20, wherein the solvent is isopropyl alcohol.

22. The method of claim 19, wherein the aqueous/solvent mixture is a 50:50 volume ratio of isopropyl alcohol and water.

23. The method of claim 1, wherein the washed precipitated xanthophylls are recovered and dried to a moisture content of less than about 1 weight %.

24. The method of claim 23, wherein the drying is by vacuum drying and/or spray drying.

25. The method of claim 1, wherein the concentration of xanthophylls is greater than 50 weight % of a composition following the recovery of the precipitated xanthophylls.

26. The method of claim 1, wherein a recovery yield of starting material trans xanthophyll is greater than 75%.

27. The method of claim 1, wherein a recovery yield of starting material trans xanthophyll is greater than 80%.

28. The method of claim 1, wherein a recovery yield of starting material trans xanthophyll is greater than 85%.

29. The method of claim 1, wherein a recovery yield of starting material trans xanthophyll is greater than 90%.

30. The method of claim 1, wherein the additional precipitated xanthophylls recovery yield exceeds 1-20% based on the amount of cis isomers in the residual liquid.

31. The method of claim 4, wherein zeaxanthin solids are formed in step (c), and wherein the zeaxanthin solids exhibit an average partit,sle size of about 60-90 microns.

32. The method of claim 4, wherein zeaxanthin solids are formed in step (c), and wherein the zeaxanthin solids exhibit a particle size of greater than 90 microns.

33. The method of claim 1, wherein the precipitated xanthophylls are micro-encapsulated as a nutritional supplement.

34. The method of claim 23, wherein the precipitated xanthophylls are in a form selected from a powder, a water-dispersible powder, and an amorphous solid.

* * * * *

UNITED STATES PATENT AND TRADEMARK OFFICE
CERTIFICATE OF CORRECTION

PATENT NO. : 8,716,533 B2
APPLICATION NO. : 13/322674
DATED : May 6, 2014
INVENTOR(S) : Joshua James Tuinstra, Gregory S. Reynhout and James Barren It is certified that error appears in the above-identified patent and that said Letters Patent is hereby corrected as shown below:

In the Claims

Column 22, Line 14: "capsanth in" should be --capsanthin--.

Column 23, Line 22: "partit,sle" should be --particle--.

Signed and Sealed this
Twelfth Day of August, 2014

Michelle K. Lee
*Deputy Director of the United States Patent and Trademark Office*